United States Patent [19]

Kraus et al.

[11] Patent Number: 5,442,072

[45] Date of Patent: Aug. 15, 1995

[54] PROCESS FOR PREPARING CHLOROMETHYLPYRIDINES

[75] Inventors: Helmut Kraus, Odenthal; Hans Lindel, Leverkusen; Hans-Joachim Diehr, Wuppertal, all of Germany

[73] Assignee: Bayer Aktiengesellschaft, Leverkusen, Germany

[21] Appl. No.: 265,526

[22] Filed: Jun. 24, 1994

[30] Foreign Application Priority Data

Jul. 2, 1993 [DE] Germany ............ 43 22 054.1

[51] Int. Cl.$^6$ ............. C07D 213/61; C07D 213/26; C07D 213/72
[52] U.S. Cl. .................... 546/345; 546/304; 546/346
[58] Field of Search ................. 546/345, 346

[56] References Cited

PUBLICATIONS

Derwent Abstract, Week 9333, KOEI E13, 93-261637/33, JP05178835-A; "Preparation of chloromethyl halo pyridine useful as ...", Koei Chem. Ind. Co.. Ltd., Dec. 26, 1991, JP 91-359435.
Chemisdjes Central-Blatt, Oct. 19, 1898, vol. II, No. 16; "Apparate"; pp. 57/887-888; "Zur Einwirkung Von Nitrosylchlori auf ...", W. Solonina.
Recueil des travaux chimiques des Pays-Bas, 1936, vol. 55, No. 17, cover page + pp. 293-294; "Das 2-(-2-pyridyl)-alanin", J. Overhoff et al.
Angewandte Chemie, Mar. 7, 1963, vol. 75, No. 5, cover page + pp. 235-240; "In der seitenkette halogenierte methylpyridine ...", W. Mathes et al.
Allied Chemical and Dye Corporation, Dec. 20, 1950, pp. 319-320/364-395; "Nitrosyl chloride", L. J. Beckham et al.

Chem. Abstracts, vol. 119, No. 17, Abst. No. 119:180.674e, Oct. 25, 1993.
J. Heterocyclic Chem., vol. 16, pp. 333-337, 1979; "Synthesis of Heterocyclic Analogs of α-Methyldopa", J. W. Tilley et al.

*Primary Examiner*—Alan L. Rotman
*Attorney, Agent, or Firm*—Sprung Horn Kramer & Woods

[57] ABSTRACT

The invention relates to a novel process for preparing chloromethylpyridines of the general formula (I)

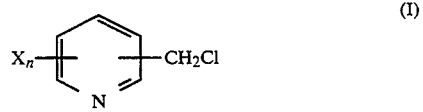

in which
  n represents the numbers 0,1,2 or 3 and
  X represents halogen, by reacting aminomethylpyridines of the general formula (II)

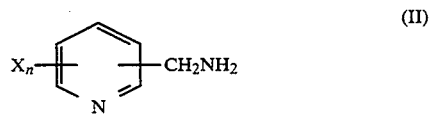

with a nitrosating or diazotizing agent in the presence of a diluent and optionally in the presence of hydrogen chloride at temperatures between −20° C. and +50° C. and then working up in a conventional manner.

1 Claim, No Drawings

PROCESS FOR PREPARING CHLOROMETHYLPYRIDINES

The invention relates to a novel process for preparing chloromethylpyridines.

It is known that chloromethylpyridines can be obtained by reaction of hydroxymethylpyridines with thionyl chloride (cf. J. Heterocycl. Chem. 16 (1979), 333–337; cf. also EP-A 373464).

It is also known that chloromethylpyridines are obtained on chlorinating methylpyridines in the presence of acid acceptors or free-radical formers and in the presence of inert diluents at temperatures between 0° C. and 100° C. (cf. EP-A 260485, cf. also EP-A 458109).

It is furthermore known that alkoxymethylpyridines too can be converted into chloromethylpyridines by reaction with suitable chlorinating agents (cf. EP-A 393453).

It has now been found that chloromethylpyridines of the general formula (I)

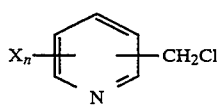

in which
n represents the numbers 0, 1, 2 or 3 and
X represents halogen, are obtained in good yields on reacting aminomethylpyridines of the general formula (II)

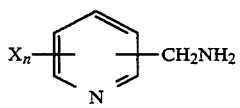

in which
n has the meaning given above and
X represents amino or halogen,
with a nitrosating or diazotizing agent in the presence of a diluent and optionally in the presence of hydrogen chloride at temperatures between −20° C. and +50° C. and then working up in a conventional manner.

Surprisingly the chloromethylpyridines of the general formula (I) can be obtained in good yields by the process of the invention.

The process of the invention preferably relates to the preparation of compounds of the formula (I) in which
n represents the numbers 0, 1 or 2 and
X represents fluorine, chlorine or bromine.

In particular, the process of the invention relates to the preparation of 3-chloromethyl-pyridine, 2-chloro-5-chloromethyl-pyridine and 2,3-dichloro-5-chloromethylpyridine.

If, for example, 3-aminomethyl-pyridine and nitrosyl chloride are used as starting materials, then the course of the reaction in the process of the invention can be shown by formulae in the following scheme:

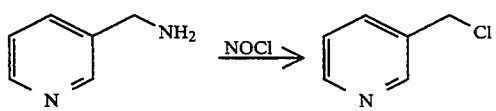

The aminomethylpyridines to be used as starting materials in the process of the invention are generally defined by the formula (II). In the formula (II), n preferably has the meaning already given as preferred for n in connection with the description of the compounds of the formula (I) to be prepared according to the invention and X preferably represents amino, fluorine, chlorine or bromine.

Examples which may be mentioned of the starting materials of the formula (II) are: 3-aminomethyl-pyridine, 2-chloro-5-aminomethyl-pyridine, 2-amino-5-aminomethyl-pyridine and 2,3-dichloro-5-aminomethyl-pyridine.

The starting materials of the formula (II) are known and/or can be prepared by processes known per se (cf. DE-OS (German Published Specification) 3726993 and WO 92/13840).

The process of the invention for preparing chloromethylpyridines of the formula (I) is carried out using a nitrosating agent or a diazotizing agent. Suitable nitrosating agents or diazotizing agents are, in particular, compounds which contain a component which can be readily cleaved off as a nitrosyl group (NO). These include, for preference, nitrosyl chloride, nitrosylsulphuric acid and dinitrogen trioxide and also alkyl nitrites such as methyl nitrite, ethyl nitrite, propyl nitrite and butyl nitrite.

Nitrosyl chloride in particular is preferred for use as nitrosating/diazotizing agent for the process of the invention.

The process of the invention is carried out in the presence of a diluent. Suitable diluents are the customary organic solvents, for example (optionally chlorinated) hydrocarbons such as pentane, hexane, heptane, octane, cyclohexane, methylcyclohexane, petroleum ether, benzine, ligroin, methylene chloride, ethylene chloride, chloroform, tetrachloromethane, chlorobenzene and o-dichlorobenzene, ethers such as diethyl ether, dipropyl ether, diisopropyl ether, dibutyl ether, diisobutyl ether, methyl tert-butyl ether, methyl tert-pentyl ether, ethylene glycol dimethyl ether, tetrahydrofuran and dioxane, ketones such as acetone, diethyl ketone, methyl isopropyl ketone and methyl isobutyl ketone, esters such as methyl acetate and ethyl acetate, nitriles such as acetonitrile and propionitrile, amides such as N,N-dimethyl-formamide, N,N-diethyl-formamide, N,N-dipropyl-formamide, N,N-dibutyl-formamide, N,N-dicyclohexyl-formamide and N,N-dimethyl-acetamide, furthermore also N-methyl-pyrrolidone, tetramethylurea, dimethyl sulphoxide, tetramethylene sulphone, liquid sulphur dioxide and water.

Two-phase systems of water and the abovementioned organic solvents, provided they are practically immiscible with water, can also be used as diluents, in which case phase transfer catalysts are preferably used. Examples of such catalysts which may be mentioned are: tetrabutylammonium bromide, tetrabutylammonium chloride, tetraoctylammonium chloride, tetrabutylammonium hydrogen sulphate, methyl-trioctylammonium chloride, hexadecyl-trimethylammonium chloride, hexadecyl-trimethylammonium bromide, benzyl-trimethylammonium chloride, benzyl-triethylammonium chloride, benzyl-trimethylammonium hydroxide, benzyl-triethylammonium hydroxide, benzyl-tributylammoninm chloride, benzyl-tributylammonium bromide, tetrabutyl-phosphonium bromide, tetrabutylphosphonium chloride, tributyl-hexadecylphosphonium bromide, butyl-triphenyl-phosphoniumchloride, ethyl-trioctylphosphoniumbromide, tetraphenylphosphoniumbromide.

The reaction temperatures in the process of the invention can be varied within a wide range. The process is generally carried out at temperatures between −20° C. and +50° C., preferably between −10° C. and +40° C.

The process of the invention is generally carried out at atmospheric pressure or at slightly increased or slightly decreased pressure, in general between 0.1 and 10 bar.

The process of the invention is carried out using generally between 1 and 5 mol, preferably between 2 and 3 mol, of nitrosating or diazotizating agent per i mol of aminomethyl-pyridine of the formula (II).

In a preferred embodiment of the process of the invention, an aminomethylpyridine of the formula (II) is initially charged in one of the abovementioned diluents and a solution of a nitrosating or diazotizing agent in one of the abovementioned diluents is metered in while stirring. The reaction mixture is then stirred until the reaction has ended; the mixture is then worked up in a conventional manner.

In a further preferred embodiment of the process of the invention, the nitrosating or diazotizing agent is initially charged in one of the abovementioned diluents, optionally in the presence of hydrogen chloride, and a solution of an aminomethylpyridine of the formula (II) in one of the abovementioned diluents is metered in while stirring. The reaction mixture is then stirred until the reaction has ended; the mixture is then worked up in a conventional manner.

The work-up can be carried out by conventional methods. For example, the reaction mixture, optionally after being concentrated, is diluted with water, neutralized with sodium hydroxide solution or sodium (hydrogen) carbonate and the organic phase optionally diluted with an organic solvent which is practically immiscible with water, for example methylene chloride. After shaking, the organic phase is separated off, dried and filtered. The organic solvent is then carefully distilled off from the filtrate under reduced pressure, the product of the formula (I) being obtained as an oily residue which can be further purified by conventional methods.

The chloromethylpyridines of the formula (I) to be prepared according to the process of the invention can be used as intermediates for the preparation of biologically active compounds, for example of insecticides (cf. EP-A 163855 and EP-A 192060).

PREPARATIVE EXAMPLES

EXAMPLE 1

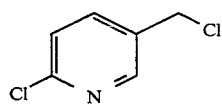

A solution of 9.2 g (141 mmol) of nitrosyl chloride in 50 ml of methylene chloride is added dropwise at 10° C. to a solution of 10.0 g (70mmol) of 2-chloro-5-aminomethylpyridine in 200 ml of methylene chloride over a period of about 90 minutes while stirring. The reaction mixture is then stirred for a further 2 hours at 20° C. 100 ml of water are subsequently added and the pH adjusted to 7 by the addition of sodium hydrogencarbonate. The organic phase is then separated off and the aqueous phase is further extracted two more times with 50 ml of methylene chloride each time. The solvent is then carefully distilled off from the combined organic phases in a water-pump vacuum.

The residue remaining contains, according to analysis by gas chromatography, 6.8 g (60% of theory) of 2-chloro-5-chloromethyl-pyridine and 3.5 g (35% of theory) of 2-chloro-5-hydroxymethyl-pyridine.

The 2-chloro-5-hydroxymethyl-pyridine obtained as by-product can be separated off by conventional methods and converted in a known manner (cf. EP-A 373464) into 2-chloro-5-chloromethyl-pyridine.

EXAMPLE 2

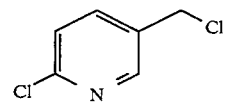

25 ml of N,N-dimethyl-formamide are saturated with hydrogen chloride at 20° C. This solution is diluted with a further 200 ml of N,N-dimethyl-formamide and, after cooling to −10° C., 20 ml of precooled nitrosyl chloride are added. The temperature of the mixture is allowed to come to 0° C. and at this temperature a solution of 17.3 g (122 mmol) of 2-amino-5-aminomethyl-pyridine in 100 ml of N,N-dimethyl-formamide is added dropwise. The reaction mixture is then allowed to come to room temperature (20° C.) and is stirred at this temperature for a further one hour. Subsequently it is concentrated in a water-pump vacuum, neutralized by addition of 50 ml of aqueous 0.2 N sodium hydroxide solution and shaken with 150 ml of methylene chloride. The organic phase is separated off, dried with sodium sulphate and filtered. The solvent is carefully distilled off from the filtrate in a water-pump vacuum.

14 g of an oil are obtained which, according to the $^1$H-NMR spectrum, contains 85% of 2-chloro-5-chloromethylpyridine (60% of theory).

We claim:
1. A process for preparing a chloromethylpyridine of the formula

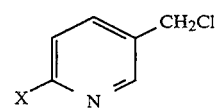

in which
X represents halogen,
wherein an aminomethylpyridine of the formula

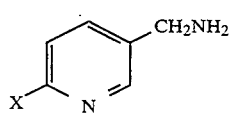

in which
X represents NH$_2$ or halogen is reacted with or nitrosylchloride in the presence of a two phase and at a temperature between −20° C. to 50° C.

* * * * *

UNITED STATES PATENT AND TRADEMARK OFFICE
CERTIFICATE OF CORRECTION

PATENT NO. : 5,442,072
DATED : August 15, 1995
INVENTOR(S) : Kraus, et al

It is certified that error appears in the above-indentified patent and that said Letters Patent is hereby corrected as shown below:

Title Page    After " [56] References Cited " insert
              -- FOREIGN PATENT DOCUMENTS:  0508215,
              10/1992, European Pat. Off. --

Col. 4, line 64   Delete " or " (second occurrence)

Signed and Sealed this

Twenty-eighth Day of November 1995

Attest:

BRUCE LEHMAN

Attesting Officer    Commissioner of Patents and Trademarks